(12) United States Patent
Zacharie et al.

(10) Patent No.: US 11,524,930 B2
(45) Date of Patent: *Dec. 13, 2022

(54) SUBSTITUTED AROMATIC COMPOUNDS AND RELATED METHOD FOR THE TREATMENT OF FIBROSIS

(71) Applicant: LIMINAL BIOSCIENCES LIMITED, Comberton (GB)

(72) Inventors: Boulos Zacharie, Laval (CA); Shaun Abbott, Pointe-Claire (CA); Lyne Gagnon, Laval (CA); Pierre Laurin, Ville Mont-Royal (CA); Brigitte Grouix, Montreal (CA)

(73) Assignee: LIMINAL BIOSCIENCES LIMITED, Comberton (GB)

( * ) Notice: Subject to any disclaimer, the term of this patent is extended or adjusted under 35 U.S.C. 154(b) by 7 days.

This patent is subject to a terminal disclaimer.

(21) Appl. No.: 16/780,316

(22) Filed: Feb. 3, 2020

(65) Prior Publication Data

US 2020/0172462 A1 Jun. 4, 2020

Related U.S. Application Data

(62) Division of application No. 15/945,408, filed on Apr. 4, 2018, now Pat. No. 10,550,066, which is a division of application No. 14/776,328, filed as application No. PCT/CA2014/000236 on Mar. 14, 2014, now Pat. No. 10,023,518.

(60) Provisional application No. 61/798,269, filed on Mar. 15, 2013.

(51) Int. Cl.
| | |
|---|---|
| *C07C 53/134* | (2006.01) |
| *C07C 57/30* | (2006.01) |
| *C07C 57/58* | (2006.01) |
| *A61K 31/192* | (2006.01) |
| *C07C 59/52* | (2006.01) |

(52) U.S. Cl.
CPC .......... *C07C 53/134* (2013.01); *A61K 31/192* (2013.01); *C07C 57/30* (2013.01); *C07C 57/58* (2013.01); *C07C 59/52* (2013.01); *Y02A 50/30* (2018.01)

(58) Field of Classification Search
CPC ....... C07C 53/134; C07C 57/30; C07C 57/58; C07C 59/52; A61K 31/192; Y02A 50/30; A61P 3/10; A61P 9/12; A61P 9/10; A61P 9/00; A61P 43/00; A61P 37/06; A61P 35/00; A61P 33/12; A61P 31/20; A61P 31/14; A61P 31/00; A61P 3/04; A61P 27/02; A61P 27/00; A61P 19/04; A61P 17/06; A61P 17/02; A61P 17/00; A61P 13/12; A61P 11/00; A61P 1/18; A61P 1/16

See application file for complete search history.

(56) References Cited

FOREIGN PATENT DOCUMENTS

| CA | 2788326 A1 | 8/2011 |
|---|---|---|
| WO | 2010127440 A1 | 11/2010 |

OTHER PUBLICATIONS

Hegazi, A. G. et al., "Inhibitory Effect of Egyptian Propolis on Fasiola gigantica Eggs with Reference to its Effect on Clostridium oedematiens and Correlation to Chemical Composition." Pakistan Journal of Biological Sciences, 2007, 10 (19): 3295-3305.

*Primary Examiner* — Kortney L. Klinkel
*Assistant Examiner* — Jason Deck
(74) *Attorney, Agent, or Firm* — Saliwanchik, Lloyd & Eisenschenk

(57) ABSTRACT

The present invention relates to compounds of:

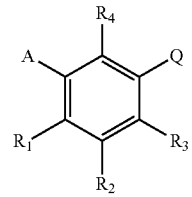

or a pharmaceutically acceptable salt thereof, wherein
A is $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4;
$R_1$ is H, F or OH;
$R_2$ is $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4;
$R_3$ is H, F, OH or $CH_2Ph$;
$R_4$ is H, F or OH;
Q is
1) $(CH_2)_m C(O)OH$ wherein m is 1 or 2,
2) $CH(CH_3)C(O)OH$,
3) $C(CH_3)_2 C(O)OH$,
4) $CH(F)-C(O)OH$,
5) $CF_2-C(O)OH$, or
6) $C(O)-C(O)OH$;
and compositions comprising the same and the method using the same for the prevention or treatment of various fibrotic diseases and conditions in subjects, including pulmonary fibrosis, liver fibrosis, skin fibrosis, renal fibrosis, pancreas fibrosis, systemic sclerosis, cardiac fibrosis or macular degeneration.

19 Claims, 1 Drawing Sheet

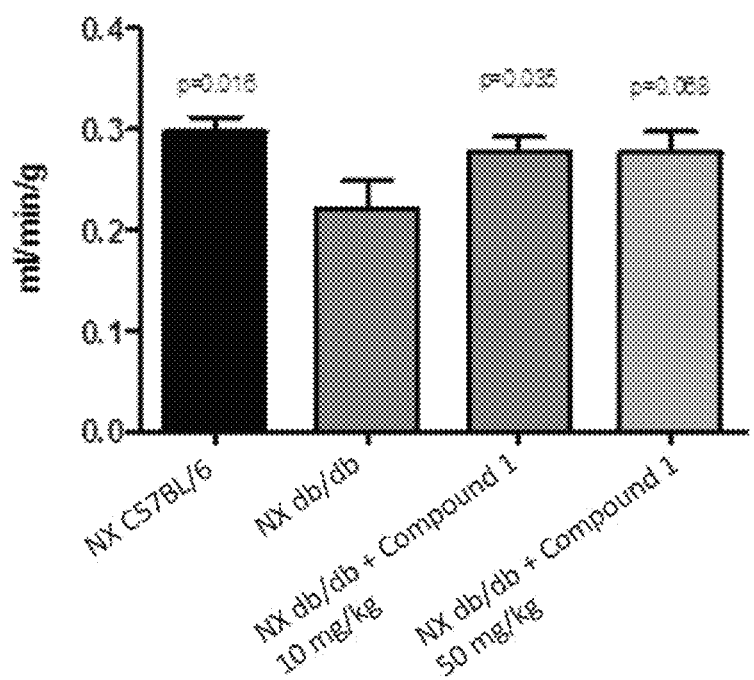

SUBSTITUTED AROMATIC COMPOUNDS AND RELATED METHOD FOR THE TREATMENT OF FIBROSIS

CROSS REFERENCE TO RELATED APPLICATIONS

This application is a division of U.S. patent application Ser. No. 15/945,408, filed Apr. 4, 2018; which is a division application of U.S. patent application Ser. No. 14/776,328, filed Sep. 14, 2015, now U.S. Pat. No. 10,023,518; which is a National Stage Application of International Application No. PCT/CA2014/000236, filed Mar. 14, 2014; which claims the benefit of U.S. Provisional Application No. 61/798,269, filed Mar. 15, 2013; all of which are incorporated herein by reference in their entirety.

FIELD OF INVENTION

The present invention relates to substituted aromatic compounds, their preparation, compositions comprising the same and the method using the same for the prevention or treatment of various fibrotic diseases and conditions in subjects, including pulmonary fibrosis, liver fibrosis, skin fibrosis, renal fibrosis, pancreas fibrosis, systemic sclerosis, cardiac fibrosis or macular degeneration.

BACKGROUND OF INVENTION

Fibrosis

Fibrosis is a chronic and progressive process characterized by an excessive accumulation of extracellular matrix (ECM) leading to stiffening and/or scarring of the involved tissue. It develops through complex cell, extracellular matrix, cytokine and growth factor interactions. Distinct cell types are involved such as resident mesenchymal cells (fibroblasts and myofibroblasts) and ECM-producing cells derived from epithelial and endothelial cells (through a process termed epithelial- and endothelial-mesenchymal transition), local or bone marrow-derived stem cells (fibrocytes). Myofibroblasts has long been regarded as a major cell type involved in normal wound healing, and as the key effector cell in fibrogenesis. They are highly synthetic for collagen and other ECM components, and are characterized by the de novo expression of α-smooth muscle actin (α-SMA) (reviewed in Scotton C. J. and Chambers R. C., 2007). The presence of myofibroblasts in fibrotic lesions in animal models of fibrosis correlates with the development of active fibrosis, and their persistence and localization to fibrotic foci in human disease is associated with disease progression (Kuhn C. and McDonald J. A., 1991, and Zhang et al., 1994). Myofibroblasts also exhibit an enhanced migratory phenotype (Suganuma et al. 1995) and are capable of releasing numerous pro-fibrotic mediators.

Fibrotic Diseases

Fibrotic diseases, including pulmonary fibrosis, systemic sclerosis, liver cirrhosis, cardiovascular disease, progressive kidney disease, and macular degeneration, are a leading cause of morbidity and mortality and can affect all tissues and organ systems. Fibrotic tissue remodeling can also influence cancer metastasis and accelerate chronic graft rejection in transplant recipients. Examples of primary (idiopathic) and secondary fibrotic disorders with multiple/single organ presentation are listed in Table 1. Nevertheless, despite its enormous impact on human health, there are currently no approved treatments that directly target the mechanism(s) of fibrosis.

TABLE 1

Examples of primary (idiopathic) and secondary fibrotic disorders with multiple/single organ presentation.

| | PRIMARY | SECONDARY |
|---|---|---|
| Heat | Idiopathic restrictive cardiomyopathy | Coronary artery disease/myocardial infarction Pressure-overload heart (long standing arterial hypertension, valvular disease) Infectious myocarditis Autoimmune diseases Transplant rejection Familial hypertrophic cardiomyopathy Arrhythmogenic right ventricular cardiomyopathy Drug-induced Post-radiation Sarcoidosis Amyloidosis |
| Kidney | Idiopathic nephrotic syndrome Idiopathic membranoproliferative glomerulonephritis | Diabetic glomerulosclerosis Hypertensive nephrosclerosis Autoimmune glomerular diseases Drug-induced Post-radiation Amyloidosis Transplant rejection |
| Systemic | Systemic sclerosis Sarcoidosis Amyloidosis | Graft versus host disease Drug-induced nephrogenic systemic fibrosis Secondary amyloidosis Post-radiation Toxic environmental exposure Storage disorders (hemochromatosis, glycogenosis, Gaucher's disease, etc.) |
| Lungs | Idiopathic pulmonary fibrosis Histiocytosis X Cryptogenic organizing pneumonia | Pneumoconiosis Infectious pneumonitis Tuberculosis Hypersensitive pneumonitis Inherited disorders |

TABLE 1-continued

Examples of primary (idiopathic) and secondary fibrotic disorders with multiple/single organ presentation.

| | PRIMARY | SECONDARY |
|---|---|---|
| Liver | Primary biliary cirrhosis<br>Primary sclerosing cholangitis | Autoimmune diseases<br>Transplant rejection<br>Drug-induced<br>Post-radiation<br>Sarcoidosis<br>Amyloidosis<br>Chronic viral hepatitis<br>Schistosomiasis<br>Alcoholic liver disease<br>Nonalcoholic fatty liver disease<br>Drug-induced<br>Toxic environmental exposure<br>Inherited metabolic disorders<br>Autoimmune hepatitis<br>Intestinal bypass |

Adapted from Vettori S, Gay S, Distler O. Role of MicroRNAs in Fibrosis, The Open Rheumatology Journal, 2012, 6, (Suppl 1: M9) 130-139.

Pulmonary Fibrosis

Lung fibrosis, also referred to as pulmonary fibrosis, is a serious medical condition that involves scarring of the lung tissue. This condition occurs when the alveoli and interstitial tissue of the lungs become inflamed and develop scars on the tissue in an attempt to repair themselves. Pulmonary fibrosis involves gradual exchange of normal lung parenchyma with fibrotic tissue (fibrous scar). The replacement of normal lung with scar tissue causes irreversible decrease in oxygen diffusion capacity. Currently, there is no cure or means by which to reverse this scarring of the lung tissue.

Pulmonary fibrosis can be caused by many conditions which includes chronic inflammatory processes (sarcoidosis, Wegener's granulomatosis), infections, environmental agents (asbestos, silica, exposure to certain gases), exposure to ionizing radiation (such as radiation therapy to treat tumors of the chest), chronic conditions (lupus), and certain medications (e.g. amiodarone, bleomycin, pingyangmycin, busulfan, methotrexate, and nitrofurantoin).

In a condition known as hypersensitivity pneumonitis, fibrosis of the lung can develop following a heightened immune reaction to inhaled organic dusts or occupational chemicals. This condition most often results from inhaling dust contaminated with bacterial, fungal, or animal products.

In some subjects, chronic pulmonary inflammation and fibrosis develop without an identifiable cause. Most of these subjects have a condition called idiopathic pulmonary fibrosis (IPF). IPF is a chronic progressive pulmonary fibrosis of unknown etiology. Prednisone is the usual treatment for IPF but it can be treated with other immunosuppressive therapies with the objective of reduction of inflammation that is the prelude to lung fibrosis. Although prednisone has a modest measurable effect on improving lung function, the scarce evidence for its long-term efficacy, as well as concerns regarding its safety, limits its use. Indeed most immunosuppressive drugs have little therapeutic effects and lung transplantation may be necessary. Unfortunately, transplants are of limited success in patients with end-stage long disease and median survival time with patients is four to six years after diagnosis. As such, there is need for novel yet efficacious treatment for IPF.

Some clinical trials are ongoing with candidate drugs that specifically address the inhibition or slowing down of fibrosis in the lungs such as interferon-γ (IFN-γ) and mycophenolate mofetil. Further examples include: pirfenidone which mechanism of action is not well defined but seems to reduce CTGF and has shown some results in clinical phase; substituted biphenyl carboxylic acids which function as lysophosphatidic acid receptor antagonists display significant antifibrotic activity in the standard pulmonary fibrosis mouse model (bleomycin-induced lung fibrosis). As such, this compound is reported to be in clinical trials for the treatment of IPF. Inhibition of protein kinase enzymes with orally active candidate drugs or treatment with orally active antioxidants provide two treatment approaches for pulmonary fibrosis: multiple receptor tyrosine kinase inhibitor (such as nintedanib) and JNK (kinase) inhibitors (such as tanzisertib). Also, drug candidates for IPF includes antioxidant N-acetylcysteine. However, to date the progress of protein kinase inhibitors and antioxidants have been questionable for the treatment of IPF due to issues of toxicity and/or efficacy. Protein kinase enzymes and associated receptors are ubiquitous amongst normal and diseased cell populations and so inhibition may result in toxicity arising in particular amongst rapidly proliferating cell populations.

Additionally, clinical trials are in progress with monoclonal antibodies that target different profibrotic proteins (cytokines (CTGF, TGF-β, MCP-1, IL-4 and IL-13), integrins (αvβ6) and enzymes (Lysyloxidase-like-2)) for the treatment of IPF. However, a number of issues are associated with the development and use of monoclonal antibodies for the treatment of IPF (which apply to other recombinant proteins) which include toxicity (including protein immunogenicity), difficulty of manufacture (batch consistency, scale-up, expense) and administration (need for refrigeration, not orally active).

Furthermore, though research trials are ongoing, there is no evidence that any medications can significantly help this condition. Lung transplantation is the only therapeutic option available in severe cases. Unfortunately, transplants are of limited success in patients with end-stage lung disease. As such, there is a need for novel yet efficacious treatments for IPF. Therefore, there is a need for novel yet conveniently administered (orally active) efficacious synthetic (readily manufactured) compounds.

Liver Fibrosis

Liver fibrosis or hepatic fibrosis is the excessive accumulation of extracellular matrix proteins (including collagen), and subsequent scarring process, that occurs in most chronic liver diseases. With time, advanced liver fibrosis results in cirrhosis of the liver. Cirrhosis is the final phase of the chronic liver disease and is generally irreversible with a poor long-term prognosis. In the advanced stage, the only option is the liver transplant. The risk of liver cancer is significant increased with cirrhosis and cirrhosis may be viewed as a premalignant condition (hepatocellular carcinoma). Indeed, cirrhosis and liver cancer are among the ten causes of death worldwide. As such, there is a need for novel yet efficacious treatment for liver fibrosis and subsequent cirrhosis of the liver. Unfortunately, few treatment options are available and most often treatment consists of addressing the causes and/or symptoms of liver cirrhosis. No treatment will cure liver fibrosis subsequent scarring and cirrhosis. Liver transplantation is the only treatment available for patients with advanced stage of fibrosis. Therefore, alternative methods that would be less intrusive are needed to cure, treat, slow the progression of, or prevent liver fibrosis.

Accumulation of fluid in the abdomen (ascites) is a common problem associated with liver cirrhosis. Treatment options include a low sodium diet, diuretics and removal of fluid by insertion of a needle into the abdominal cavity (paracentesis). Cirrhosis of the liver is caused by alcohol abuse, viral hepatitis (B, C and D), non-alcoholic fatty liver disease (NAFLD) associated with obesity, diabetes, protein malnutrition, coronary artery disease, corticosteroids, auto-immune hepatitis, inherited diseases (cystic fibrosis, alpha-1-antitrypsin deficiency, etc), primary biliary cirrhosis, drug reaction and exposure to toxins.

A limited number of clinical trials are in progress with candidate drugs that specifically address the inhibition or slowing down of fibrosis in the liver. However, these trials target specific liver disease such as NASH (Non-alcoholic Steatohepatitis). NASH refers to a combination of fatty liver (NAFLD) with inflammation and occurs in individuals who drink little or no alcohol. Cysteamine is a precursor of the potent liver antioxidant glutathione and increased in vivo production of glutathione is believed to offer improvement of NASH-related liver disease. As such, cysteamine is under evaluation in clinical trial in pediatric patients with NASH. Other antioxidants are under evaluation such as vitamin E and selenium but their effectiveness for the treatment of NASH is unknown. Also under evaluation for the treatment of NASH is the use of anti-diabetic drugs even in patients without diabetes. This approach addresses the fact that most NASH patients have insulin resistance. Once again, there is a need for novel yet conveniently administered (orally active) efficacious compound for the treatment of liver fibrosis, subsequent scarring and liver cirrhosis.

Skin Fibrosis

Skin fibrosis or dermal fibrosis is excessive scarring of the skin, and is a result of a pathologic wound healing response. There is a wide spectrum of fibrotic skin diseases: scleroderma, nephrogenic fibrosing dermopathy, mixed connective tissue disease, scleromyxedema, scleredema, and eosinophilic fasciitis. Exposure to chemicals or physical agents (mechanical trauma, burn wounds) are also potential causes of fibrotic skin disease. Dermal fibrosis may be driven by immune, autoimmune, and inflammatory mechanisms. The balance of collagen production and degradation by fibroblasts plays a critical role in the pathophysiology of fibrotic processes in the skin. Certain cytokines promote would healing and fibrosis, such as transforming growth factor-$\beta$ (TGF-$\beta$) and interleukin-4 (IL-4), whereas others are antifibrotic, such as interferon-$\gamma$ (IFN-$\gamma$) and tumor necrosis factor-$\alpha$ (TNF-$\alpha$). Fibroblasts of normal skin are quiescent. They synthesize controlled amounts of connective tissue proteins and have low proliferative activity. Following skin injury, these cells become activated, i.e. they proliferate, express $\alpha$-smooth muscle actin ($\alpha$-SMA) and synthesize large amounts of connective tissue proteins. The activated cells are often called myofibroblasts.

Scar formation as part of the wound healing process and which accompanies fibrosis is particularly undesired from a cosmetic perspective during skin fibrosis, especially when the scars are formed on the face and/or other exposed parts of the body. Scleroderma refers to skin fibrosis; sclera=hard and derma-skin. However, skin fibrosis may have important health consequences, especially if it is part of systemic scleroderma. The latter refers to a connective tissue disease of auto-immune etiology. Whereas limited cutaneous scleroderma is restricted to skin on the face and on feet, diffuse cutaneous scleroderma covers more of the skin and may progress to the visceral organs.

The most popular approach for treating skin fibrosis is the use of immunosuppressive therapy. The rationale is that the auto-immune etiology is responsible for the inflammation aspect of the disease along with subsequent tissue damage and fibrosis. Studied drugs include methotrexate, mycophenolate, mofetil, cyclophosphamide and cyclosporine. Although some improvement has been observed with immunosuppressive therapy, concerns regarding drug safety along with a lack of definitive clinical data and demonstratable efficacy, remain.

There is a need to develop efficacious pharmaceutical preparation for treating skin fibrosis, fibrotic skin diseases and pathological scarring of the skin.

Renal Fibrosis

The kidney is a structurally complex organ that has evolved to perform a number of important functions: excretion of the waste products of metabolism, regulation of body water and salt, maintenance of appropriate acid balance, and secretion of a variety of hormones and autocoids. Diseases of the kidney are as complex as its structure, but their study is facilitated by dividing them by their effects on four basic morphologic components: glomeruli, tubules, interstitium, and blood vessels. Unfortunately, some disorders affect more than one structure and the anatomic interdependence of structures in the kidney implies that damage to one almost always secondarily affects the others. Thus, whatever the origin, there is a tendency for all forms of renal disease ultimately to destroy all four components of the kidney, culminating in chronic renal failure. For instance, in auto-immune diseases such as diabetes mellitus, the kidneys are prime targets to suffer tissue damage or lesions. Nephrectomy, or kidney removal, a procedure which is sometimes performed on patients with kidney cancer (e.g. renal cell carcinoma), and may negatively impact kidney function in the remaining kidney. Chemotherapy and immunosuppressive therapy are also a source of harmful effects to the kidneys. All these kidney injuries result in most of the cases in renal fibrosis. The term "renal fibrosis" means excessive proliferation of cells, hardening tissue and scarring. Renal fibrosis can also result from dialysis following kidney failure and catheter placement, e.g., peritoneal and vascular access fibrosis. Renal fibrosis may also result from a nephropathy such as glomerular diseases (e.g. glomerulosclerosis, glomerulonephritis), chronic renal insufficiency, acute kidney injury, end stage renal disease and renal failure. Regardless of etiology, all patients with chronic renal disease show a progressive decline in renal function with time. Fibrosis, so-called scarring, is a key cause of this pathophysiology. Fibrosis involves an excess accumulation of extracellular matrix (primarily composed of collagen) and usually results in loss of function when normal tissue is replaced with scar tissue. The process is largely irreversible, inevitably leading to end-stage renal failure, a condition that requires life-long dialysis or renal transplantation. Recent major advances have led to a much better understanding of renal fibrosis (or renal tubulointerstitial fibrosis), many problems remain. Little is known about why some wounds heal and others scar and little about how many putative antifibrotic agents work.

There is a need to develop efficacious pharmaceutical preparation for treating renal fibrosis.

Cardiac Fibrosis

Cardiac fibrosis, a hallmark of heart disease, is thought to contribute to sudden cardiac death, ventricular tachyarrhythmia, left ventricular (LV) dysfunction, and heart failure. Cardiac fibrosis is characterized by a disproportionate accumulation of fibrillated collagen that occurs after myocyte death, inflammation, enhanced workload, hypertrophy, and stimulation by a number of hormones, cytokines, and growth factors.

Cardiac fibrosis may also refer to an abnormal thickening of the heart valves due to inappropriate proliferation of cardiac fibroblasts but more commonly refers to the proliferation of fibroblasts in the cardiac muscle. Fibrocyte cells normally secrete collagen, and function to provide structural support for the heart. When over-activated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

The most obvious treatment for cardiac valve fibrosis or fibrosis in other locations, consists of stopping the stimulatory drug or production of serotonin. Surgical tricuspid valve replacement for severe stenosis (blockage of blood flow) has been necessary in some patients. Also, a compound found in red wine, resveratrol, has been found to slow the development of cardiac fibrosis. [Olson et al. (2005) "Inhibition of cardiac fibroblast proliferation and myofibroblast differentiation by resveratrol". American journal of physiology. Heart and circulatory physiology 288 (3): H1131-8; Aubin, et al. (2008) "Female rats fed a high-fat diet were associated with vascular dysfunction and cardiac fibrosis in the absence of overt obesity and hyperlipidemia: Therapeutic potential of resveratrol". The Journal of Pharmacology and Experimental Therapeutics 325 (3): 961-8. More sophisticated approaches of countering cardiac fibrosis like microRNA inhibition (miR-21, for example) are being tested in animal models.

No medication is on the market to prevent or treat cardiac fibrosis and there is a need to develop efficacious pharmaceutical preparation.

Pancreatic Fibrosis

Chronic pancreatitis (CP) is a progressive inflammatory disease of the pancreas, characterized by irreversible morphologic changes and gradual fibrotic replacement of the gland. Loss of exocrine and endocrine function results from parenchymal fibrosis. The primary symptoms of CP are abdominal pain and maldigestion. Grossly, the pancreas may be enlarged or atrophic, with or without cysts or calcifications or tumors. The ducts may be dilated, irregular, or strictured. Essential pathologic features include irregular and patchy loss of acinar tissue, chronic inflammation, ductal changes, and fibrosis. These gross changes are end-manifestations of complex pathogenic mechanisms that are associated with gene mutations (including but not limited to cystic fibrosis, cationic trypsinogen gene, CFTR gene mutations in idiopathic acute and chronic pancreatitis, the pancreatic secretory trypsin inhibitor gene, the chymotrypsinogen C gene and the calcium sensing receptor gene, alpha-1 antitrypsine deficiency), metabolic (alcoholic, tobacco smoking, hypercalcemia, hyperlipidemia, chronic renal failure), environmental factors (nutritional factors such as micronutrient dificiencies (zinc, copper and selenium; also by postadiation exposure), obstructive (tumors), ischemic (vascular diseases), and autoimmune or associated with primary sclerosing cholangitis, Sjögren's syndrome, primary biliary disorder and type 1 diabetes mellitus. Because of diagnostic and therapeutic challenges, an interdisciplinary management strategy is required.

Macular Degeneration

Most diseases that cause catastrophic loss of vision (e.g. macular degeneration) do so as a result of abnormal angiogenesis and wound healing, often in response to tissue ischemia or inflammation. Disruption of the highly ordered tissue architecture in the eye caused by vascular leakage, hemorrhage, and concomitant fibrosis can lead to mechanical disruption of the visual axis and/or biological malfunctioning. The CNS is highly specialized in many ways, including the types of inflammatory and wound-healing cells present. Since the retina is part of the CNS, its response to injury utilizes mechanisms very similar to those observed in the rest of the brain; this is true not only for the wound-healing response but also for utilization of migratory cues functional during development of the neuronal and vascular component of this highly organized tissue (Friedlander M.; Fibrosis and diseases of the eye, J. Clin. Invest. 2007). As discussed below, the response of the anterior segment of the eye to wound healing more closely resembles the response of non-CNS tissues than do such events in the posterior segment or the eye. Therefore, I refer to such wound-healing events in the anterior segment as fibrosis, whereas comparable events in the retina are referred to as gliosis. Although such distinction is somewhat artificial, it does serve to differentiate between the fibroblasts and glial cells that effect the wound-healing and scar-formation events. An increased understanding of inflammation, wound healing, and angiogenesis has led to the development of drugs effective in modulating these biological processes and, in certain circumstances, the preservation of vision. Unfortunately, such pharmacological interventions often are too little, too late, and progression of vision loss frequently occurs.

There is need to prevent or treat each fibrotic disease with a safe and efficacious drug.

SUMMARY OF THE INVENTION

More particularly, the present invention concerns novel substituted aromatic compounds as defined by the formula herein below. Compared to known aromatic compounds, the present compounds have a longer chain at position $R_2$; and this particularity of the present compounds has shown to have favorable and surprising impact on the activity. Therefore, the present invention concerns a compound defined by formula:

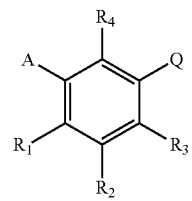

or a pharmaceutically acceptable salt thereof, wherein

A is $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4; or is preferably $C_5$ alkyl, $C_5$ alkenyl, $C(O)-(CH_2)_n-CH_3$ or $CH(OH)-(CH_2)_n-CH_3$ wherein n is 3; or is preferably $C_6$ alkyl, $C_6$ alkenyl, $C(O)-(CH_2)_n-CH_3$ or $CH(OH)-(CH_2)_n-CH_3$ wherein n is 4;

$R_1$ is H, F or OH; or is preferably H or OH;

$R_2$ is $C_5$ alkyl, $C_6$ alkyl, $C_5$ alkenyl, $C_6$ alkenyl, $C(O)-(CH_2)_n-CH_3$ or $CH(OH)-(CH_2)_n-CH_3$ wherein n is 3 or 4; or is preferably $C_5$ alkyl, $C_5$ alkenyl, $C(O)-(CH_2)_n-CH_3$ or $CH(OH)-(CH_2)_n-CH_3$ wherein n is 3; or is preferably $C_6$ alkyl, $C_6$ alkenyl, $C(O)-(CH_2)_n-CH_3$ or $CH(OH)-(CH_2)_n-CH_3$ wherein n is 4;

$R_3$ is H, F, OH or $CH_2Ph$; or is preferably H, F or OH; or is preferably H or OH;

$R_4$ is H, F or OH; or is preferably H or OH;

Q is
1) $(CH_2)_mC(O)OH$ wherein m is 1 or 2,
2) $CH(CH_3)C(O)OH$,
3) $C(CH_3)_2C(O)OH$,
4) $CH(F)-C(O)OH$,
5) $CF_2-C(O)OH$, or
6) $C(O)-C(O)OH$.

In a preferred embodiment, the pharmaceutically acceptable salt of the compound is sodium, potassium, lithium, ammonium, calcium, magnesium, manganese, zinc, iron, or copper. The preferred pharmaceutically acceptable salt of the compound is sodium.

A preferred compound according to the present invention is one of the following compounds:

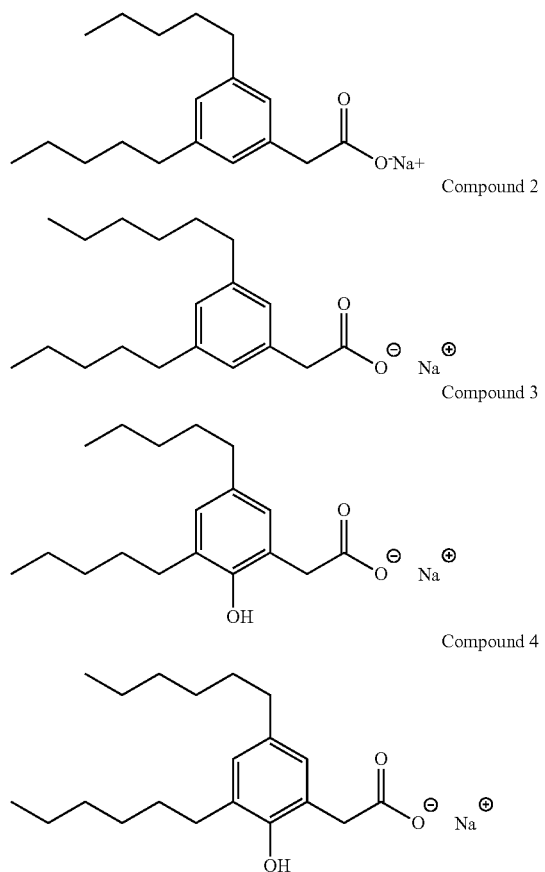

Compound 1

Compound 2

Compound 3

Compound 4

-continued

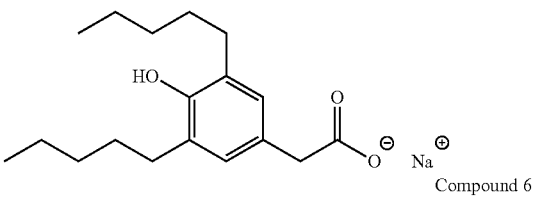

Compound 5

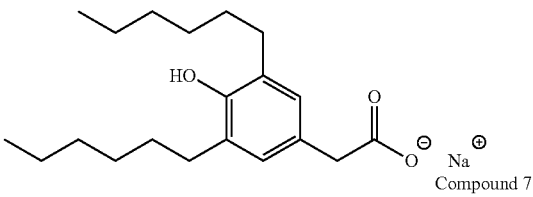

Compound 6

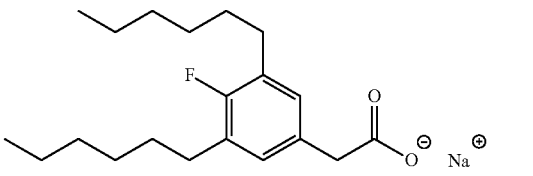 [SMILES: CCCCCCc1cc(CCCCCC)cc(CC(=O)[O-])c1 ; [Na+]]

Compound 7

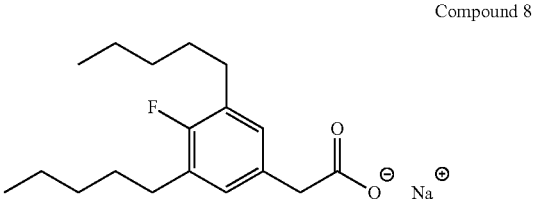

Compound 8

The present invention also concerns a method for reducing the collagen production in cells, comprising contacting the cells with a therapeutically effective amount of a compound of the present invention. The collagen is preferably collagen 1. The collagen production is preferably the collagen mRNA expression and the production of the collagen protein. According to a preferred embodiment, the cells are in culture, are part of an organ or are part of an organ that is entirely part of a live animal, where said animal includes, without limitation, a mouse, a rat or a human. In the case that the cells are part of an organ that is entirely part of a live animal, the step of contacting the cells with a therapeutically effective amount of a compound of the present invention is equivalent to administering the compound to the animal. In the case that the cells are part of an organ that is entirely part of a live animal and the live animal is a human, the therapeutically effective amount of a compound corresponds to a topical administration of preferably between about 0.01 to about 10% (w/w), or between about 0.1 to 10% (w/w), or between about 1.0 to about 10% (w/w), between about 0.1 to about 5% (w/w), or between about 1.0 to about 5% (w/w), or to an oral administration of preferably between about 1 to about 50 mg/kg, or between about 1 to 25 mg/kg, or between about 1 to about 10 mg/kg, between about 5 to about 25 mg/kg, or between about 10 to about 20 mg/kg. In the case of cultured cells, the therapeutically effective amount of a compound corresponds to 0.01 to 0.5 mM, and preferably of about 0.2 mM.

The present invention further concerns a method for preventing and/or slowing progression of and/or treating a fibrotic disease in a subject in need thereof, comprising the administration of a therapeutically effective amount of the compound of the present invention. In a preferred embodiment of the invention, the fibrotic disease is pulmonary fibrosis, liver fibrosis, skin fibrosis, renal fibrosis, pancreas fibrosis, systemic sclerosis, cardiac fibrosis or macular degeneration.

The compound is preferably administered orally. The subject is preferably a human. When compound is administered orally and the subject is a human, the therapeutically effective amount is preferably between about 1 to about 50 mg/kg, or between about 1 to about 25 mg/kg or between about 5 to about 25 mg/kg, or between about 1 to about 20 mg/kg, or between about 1 to about 10 mg/kg, or between about 10 to 20 mg/kg.

According to a preferred embodiment of the invention, the fibrotic disease is pulmonary fibrosis. The pulmonary fibrosis is preferably idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension.

In an embodiment, the fibrotic disease is liver fibrosis. According to a preferred embodiment of the invention, the liver fibrosis is resulting from a chronic liver disease, hepatitis B virus infection, hepatitis C virus infection, hepatitis D virus infection, schistosomiasis, alcoholic liver disease or non-alcoholic steatohepatitis, obesity, diabetes, protein malnutrition, coronary artery disease, auto-immune hepatitis, cystic fibrosis, alpha-1-antitrypsin deficiency, primary biliary cirrhosis, drug reaction and exposure to toxins.

In an embodiment, the fibrotic disease is skin fibrosis. According to a preferred embodiment of the invention, the skin fibrosis is scarring, hypertrophic scarring, keloid scarring, dermal fibrotic disorder, wound healing, delayed wound healing, psoriasis or scleroderma. Said scarring may derived from a burn, a trauma, a surgical injury, a radiation or an ulcer. Said ulcer can be a diabetic foot ulcer, a venous leg ulcer or a pressure ulcer.

When the fibrotic disease is a skin fibrosis, the compound is preferably administered topically or orally. When the compound is administered topically and the subject is human, the therapeutically effective amount of the compound of the present invention is preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). When administered orally, the therapeutically effective amount of the compound of the present invention is preferably between about 1 to about 50 mg/kg, or between about 1 to 25 mg/kg, or between about 1 to about 10 mg/kg, between about 5 to about 25 mg/kg, or between about 10 to about 20 mg/kg, and the subject is human.

In an embodiment, the fibrotic disease is kidney fibrosis. According to a preferred embodiment of the invention, the kidney fibrosis is resulting from dialysis following kidney failure, catheter placement, a nephropathy, glomerulosclerosis, glomerulonephritis, chronic renal insufficiency, acute kidney injury, end stage renal disease or renal failure.

According to a preferred embodiment, the invention also concerns a method for antagonizing collagen secretion or collagen deposition in an organ, such as the lung, the liver, the skin or the heart, of a mammal comprising the administration of a therapeutically effective amount of a compound of the present invention to the mammal that is in need thereof, wherein the organ is kidney, lung, liver, skin or heart. The mammal that is in need thereof is a mammal that is subject to an excessive collagen secretion or collagen deposition in an organ such as the kidney, the lung, the liver, the skin or the heart. Usually, the excessive collagen secretion or collagen deposition in an organ results from an injury or an insult. Such injury and insult are organ-specific and are described herein in details in the background section and in the whole specification. The therapeutically effective amount described hereinabove in detail also applies to the present method for antagonizing collagen secretion or collagen deposition in an organ. The route of administration described herein also applies to the present method. The compound is preferably administered over a sufficient period of time to antagonize the level of collagen deposition in the organ, completely or partially. The term "antagonizing" used herein is intended to mean "decreasing" or "reducing". A sufficient period of time can be during one week, or between 1 week to 1 month, or between 1 to 2 months, or 2 months or more. For chronic condition, the compound of the present invention can be advantageously administered for life time period.

In an embodiment, the fibrotic disease is cardiac fibrosis. In this embodiment, the therapeutically effective amount is preferably between about 1 to about 50 mg/kg, and preferably or between about 1 to 25 mg/kg, or between about 1 to about 10 mg/kg, between about 5 to about 25 mg/kg, between about 5 to about 20 mg/kg, or between about 10 to about 20 mg/kg. The compound is preferably administered orally. The subject is preferably a human.

In another preferred embodiment, the compound of the present invention can be administered in combination with a therapeutically effective amount of second compound where the second compound is preferably a therapeutic agent know for being effective in preventing or treating or potentially preventing or treating a fibrotic disease. According to an embodiment of the present invention, the compound can be administered in combination with a therapeutically effective amount of second compound, the second compound is an immunosuppressive drug, an anti-inflammatory drug, a cytokine, a monoclonal antibody, a multiple receptor tyrosine kinase inhibitor, an antioxidant, an enzyme inhibitor, an integrin inhibitor, an hypertensive inhibitor, a lipid receptor modulator or a thiazolindione.

In addition to the previous embodiments of dosages, for all above mentioned fibrotic diseases, when the compound of the present invention is orally administered to a human, the therapeutically effective amount of a compound corresponds to preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). In all above mentioned fibrotic diseases, when the compound of the present invention is orally administered to a human, the therapeutically effective amount of a compound corresponds preferably between about 1 to about 50 mg/kg, or between about 1 to 25 mg/kg, or between about 1 to about 10 mg/kg, between about 5 to about 25 mg/kg, or between about 10 to about 20 mg/kg.

The present invention also concerns a kit for preventing and/or slowing progression of and/or treating fibrotic disease in a subject in need thereof. The kit comprises a compound represented by the formula:

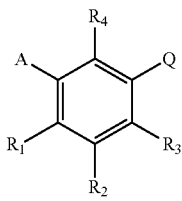

or a pharmaceutically acceptable salt thereof, wherein

A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4;

$R_1$ is H, F or OH; or is preferably H or OH;

$R_2$ is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4;

$R_3$ is H, F, OH or $CH_2Ph$; or is preferably H, F or OH; or is preferably H or OH;

$R_4$ is H, F or OH; or is preferably H or OH;

Q is
1) $(CH_2)_m C(O)OH$ wherein m is 1 or 2,
2) $CH(CH_3)C(O)OH$,
3) $C(CH_3)_2 C(O)OH$,
4) $CH(F)$—$C(O)OH$,
5) $CF_2$—$C(O)OH$, or
6) $C(O)$—$C(O)OH$;

and instructions for administering a therapeutically effective amount of the compound to the subject suffering from said fibrotic disease. In a preferred embodiment of the invention, the fibrotic disease is pulmonary fibrosis, liver fibrosis, skin fibrosis, renal fibrosis, pancreas fibrosis, systemic sclerosis, cardiac fibrosis or macular degeneration. The kit may also comprises instructions for administering any of the above-disclosed therapeutically effective amount of the compound for oral administration.

For all fibrotic diseases, the kit preferably further comprises instructions for administering between about 1 to about 50 mg/kg of the compound daily and orally to the subject who is a human.

When the fibrotic disease is skin fibrosis, the kit preferably further comprises instructions suggesting administering topically and daily between about 0.01 to about 10% (w/w) of the compound to the subject who is a human; or instructions suggesting administering orally and daily between about 1 to about 50 mg/kg of the compound to the subject who is a human.

BRIEF DESCRIPTION OF THE FIGURES

FIG. 1 illustrates the glomerular filtration rate (GFR) function in db/db diabetic mouse compared to C57BL/6 mice (control mice), and in db/db diabetic mouse following oral treatment with Compound 1 at a dose of 10 and 50 mg/kg.

DETAILED DESCRIPTION OF THE INVENTION

As used herein, the term "alkyl" is intended to include both branched and straight chain saturated aliphatic hydrocarbon groups having five or six carbon atoms. Examples of alkyl defined above include, but are not limited to, n-pentyl, n-hexyl, isopentyl, isohexyl, t-pentyl and t-hexyl. Similarly, as used herein, the term "alkenyl" is intended to include unsaturated straight or branched chain hydrocarbon groups having five or six carbon atoms, and in which at least two carbon atoms are bonded to each other by a double bond, and having E or Z regiochemistry and combinations thereof. Examples of alkenyl defined above include, but are not limited to, 1-pentenyl, 2-pentenyl, 1-hexenyl and 2-hexenyl.

The compounds of the present invention, or their pharmaceutically acceptable salts may contain one or more asymmetric centers, chiral axes and chiral planes, and may thus give rise to enantiomers, diastereomers and other stereoisomeric forms and subsequently may be defined in terms of absolute stereochemistry such as (R)- or (S)-. The present invention is therefore intended to include all such possible isomers, as well as their racemic and optically pure forms. Optically active (+) and (−), (R)- and (S)-, or (D)- and (L); isomers may be prepared using chiral synthons or chiral reagents or resolved using conventional techniques, such as reverse phase HPLC. The racemic mixtures may be prepared and subsequently separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, or selective reaction of one enantiomer with an enantiomer specific reagent.

As used herein, the term "pharmaceutically acceptable salt" is intended to mean those salts which retain the biological effectiveness and properties of the free acids, which are not biologically or otherwise undesirable. These salts are derived from addition of an inorganic base or an organic base to the organic acid. Salts prepared from inorganic bases include, but are not limited to, the sodium, potassium, lithium, ammonium, calcium, magnesium, manganese, zinc, iron, copper and the like. Salts prepared from organic bases include, but are not limited to, salts of primary, secondary and tertiary amines, substituted amines including naturally occurring substituted amines, cyclic amines and basic amino acids (lysine, arginine, and histidine). Examples of pharmaceutically acceptable salts are also described, for example, in Berge et al., "Pharmaceutical Salts", J. Pharm. Sci. 66, 1-19 (1977). Preferred salt of the compound of the present invention are sodium, potassium, lithium, ammonium, calcium and magnesium; and more preferably sodium. Pharmaceutically acceptable salts may be synthesized from the parent compound that contains an acid moiety by conventional chemical methods. Generally, such salts are prepared by reacting the free acid form of these compounds with a stoichiometric amount of the appropriate base in water or in an organic solvent, or in an aqueous/organic solvent mixture. Salts may be prepared in situ, during the final isolation or purification of the compound or by separately reacting the purified compound of the invention in the free acid form with the desired corresponding base, and isolating the product salt.

As indicated herein above and exemplified herein below, the compound of the invention has beneficial pharmaceutical properties and may have useful pharmaceutical applications in the prevention and/or treatment of various fibrotic diseases and related conditions in a subject. Medical and pharmaceutical applications contemplated by the inventors include, but are not limited to, those addressing pulmonary fibrosis, liver fibrosis, skin fibrosis, renal fibrosis, pancreas fibrosis, systemic sclerosis, cardiac fibrosis or macular degeneration.

The term "subject" includes living organisms in which a fibrotic disease can occur, or which are susceptible to such a condition. The term "subject" includes animals such as mammals or birds. Preferably, the subject is a mammal. More preferably, the subject is a human. Even more preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The present invention relates to methods, compounds, compositions and kit for preventing and/or treating a fibrotic disease.

The term "fibrotic disease" means any fibrosis or disease characterized by an excess accumulation of extracellular matrix (primarily composed of collagen) and which results in loss of function when normal tissue is replaced with scar tissue. The fibrotic disease includes, without limitation, pulmonary fibrosis, liver fibrosis, skin fibrosis, renal fibrosis, pancreas fibrosis, systemic sclerosis, cardiac fibrosis and macular degeneration.

The term "pulmonary fibrosis" or "lung fibrosis" means the formation or development of excess fibrous connective tissue (fibrosis) in the lung thereby resulting in the development of scarred (fibrotic) tissue. More precisely, pulmonary fibrosis is a chronic disease that causes swelling and scarring of the alveoli and interstitial tissues of the lungs. The scar tissue replaces healthy tissue and causes inflammation. This chronic inflammation is, in turn, the prelude to fibrosis. This damage to the lung tissue causes stiffness of the lungs which subsequently makes breathing more and more difficult.

Pulmonary fibrosis is a complicated illness that can arise from many different causes which include microscopic damage to the lungs induced by inhalation of small particles (asbestos, ground stone, metal dust, particles present in cigarette smoke, silica dust, etc). Alternatively, pulmonary fibrosis may arise as a secondary effect of other diseases (autoimmune disease, viral or bacterial infections, etc). Certain drugs such as cytotoxic agents (e.g. bleomycin, busulfan and methotrexate); antibiotics (e.g. nitrofurantoin, sulfasalazine); antiarrhitmics (e.g. amiodarone, tocainide); anti-inflammatory medications (e.g. gold, penicillamine); illicit drugs (e.g. crack cocaine, heroin); also can cause pulmonary fibrosis. However, when pulmonary fibrosis appears without a known cause, it is termed as "idiopathic" or idiopathic pulmonary fibrosis (IPF).

Pulmonary fibrotic disorders is thought to begin with acute injury to the pulmonary parenchyma, leading to chronic interstitial inflammation, then to fibroblast activation and proliferation, and finally progressing to the common endpoint of pulmonary fibrosis and tissue destruction. Current research indicates that inflammation is less important in IPF, which appears to be primarily a disorder of fibroblast activation and proliferation in response to some as yet unknown trigger(s). Broadly, the manifestations of fibrotic lung disease can be grouped as follows: they may be chronic, insidious, and slowly progressive; they may be subacute, with a resolving, remitting, relapsing, or progressive course; and they may be acute, with a fulminant, progressive, remitting, or resolving course. Disorders with chronic, insidious, and slowly progressive courses are those that clinically resemble IPF and usually share a common pathology (ie, UIP). Many of the connective-tissue diseases (e.g. rheumatoid arthritis; CREST syndrome (calcinosis cutis, Raynaud's syndrome, esophageal motility disorder, sclerodactyly, and telangiectasia); syndrome/progressive systemic scleroderma; systemic lupus erythematosus; mixed connective-tissue disease; pneumoconioses (e.g. asbestosis, silicosis); chronic hypersensitivity pneumonitis; and drug-related pulmonary fibrosis (e.g. due to bleomycin) generally fit into this category. Development of clinically apparent lung diseases related to occupational exposures (e.g. pneumoconiosis) generally occurs many years after the exposure. Radiation fibrosis often develops months to years after radiation exposure. A lag time of months or years can occur between the use of pulmonary toxic medications and the development of fibrotic disease. The effect can be dose-dependent (e.g. bleomycin), although, in other cases, the relationship is less clear. Pulmonary manifestations of connective-tissue disease may develop in advance of, coincident with, or many years after the onset of articular disease. Pulmonary sarcoidosis, although sometimes acute or subacute in onset, in some cases may present insidiously over time. Subacute presentations with a variable course are typified by cryptogenic organizing pneumonia (COP). COP often develops weeks or months after the onset of a flulike illness. The course is variable and may either spontaneously remit or progress. The disorder is thought to be very responsive to steroid therapy, although it may recur when steroids are withdrawn or tapered. In some cases, COP may progress to end-stage fibrotic lung disease. Disorders with an acute onset are typified by acute interstitial pneumonitis (AIP), which is an idiopathic form of severe lung injury. The histopathology is that of adult respiratory distress syndrome with diffuse alveolar damage. Patients present either with no antecedent history of lung disease or as part of an accelerated phase of underlying interstitial disease. Most patients progress rapidly to respiratory failure. Some patients may improve with steroids or other immunosuppressive therapy.

The term "liver fibrosis" means the formation or development of excess fibrous connective tissue (fibrosis) in the liver thereby resulting in the development of scarred (fibrotic) tissue. The scarred tissue replaces healthy tissue by the process of fibrosis and leads to subsequent cirrhosis of the liver and to hepatocellular carcinoma.

The term "skin fibrosis" or "dermal fibrosis" means the excessive proliferation of epithelial cells or fibrous connective tissue (fibrosis) thereby resulting in the development of scarred (fibrotic) tissue. The scarred tissue replaces healthy tissue by the process of fibrosis and may be the prelude of systemic scleroderma. Skin fibrosis is intended to cover the fibrosis of any skin tissue and epithelial cells including, without limitation, blood vessels and veins, internal cavity of an organ or a gland such as ducts of submandibular, gallbladder, thyroid follicles, sweat gland ducts, ovaries, kidney; epithelial cells of gingival, tongue, palate, nose, larynx, oesophagus, stomach, intestine, rectum, anus and vagina; derma, scar, skin and scalp. The compounds of the present invention are active for promoting healing of wound and one or more of the following activities:

improving collagen organization and/or reducing wound cellularity in said wound;

reducing collagen overproduction by fibroblast and epithelial cells in said wound;

reducing epithelial mesenchymal transition in said wound;

reducing fibroblast migration and activation in said wound;

reducing and/or inhibiting dermal thickening in said wound;

reducing and/or inhibiting recruitment of inflammatory cells to said wound.

In general, prophylactic and therapeutic uses comprise the administration of a compound as described herein to a subject, preferably a human patient in need thereof. The compounds according to the invention may be administered in combination with a therapeutically effective amount of a second compound which can be comprised in the same pharmaceutical composition or in a second pharmaceutical composition. The second compound is advantageously an immunosuppressive drug including, but not limited to, cyclosporine, azathioprine, cyclophosphamide, or mycophenolate mofetil; an anti-inflammatory drug including, but not limited to, a corticosteroid (e.g. prednisone), a cytokine including but not limited to, interferon-alpha, interferon gamma, interleukine 12; a monoclonal antibody including but not limited to CTGF, TGF-β, MCP-1, IL-4 and IL-13; a multiple receptor tyrosine kinase inhibitor including, but not limited to, Nintedanib and the JNK (kinase) inhibitor Tanzisertib (CC-930); an antioxidant such as, but not limited to, N-acetylcysteine, pirfenidone, vitamin E, S-adenosyl methionine, or penicillamine; an enzyme inhibitor including, but not limited, to Lysyloxidase-like-2 (LOXL2 enzyme); an integrin inhibitor such as, but not limited to, $\alpha_v\beta_6$; a lipid receptor modulator including, but not limited to, lysophosphatidic acid receptor antagonists; pirfenidone, or a thiazolindione.

A related aspect of the invention concerns pharmaceutical compositions and kits which comprise one or more of the compounds of the invention described herein. As indicated herein above, the compounds of the invention may be useful in preventing and/or treating a fibrotic disease.

A related aspect of the invention concerns the prophylactic and therapeutic uses of a compound in related to a fibrotic disease.

Pulmonary fibrosis can lead to several severe complications. Because the fibrotic lungs have impaired oxygen intake capacity, low blood oxygen levels (hypoxemia) can develop. Lack of oxygen can affect the entire body. Another complication of pulmonary fibrosis is pulmonary hypertension (high blood pressure in the arteries of the lungs). Scar tissue in the lungs can make it more difficult for blood to flow through them. The increased pressure makes the heart work harder and leads to a weakened and enlarged heart, reducing its pumping efficiency and producing heart failure. This is suspected when people develop fluid accumulations in the abdomen, leg swelling, or prominent pulsations in neck veins.

Liver fibrosis can lead to severe malfunction of the liver and can result in complete non-functioning of the liver.

Skin fibrosis can lead to hash mark, permanent cicatrix and scar causing severe esthetic problems and stiffness of the skin following a skin injury from a surgery or an accident.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g., bioavailability, stability, potency, toxicity, etc.), and the particular disorder(s) the subject is suffering from. In addition, the therapeutically effective amount that is administered intravenously may depend on the subject's blood parameters e.g., lipid profile, insulin levels, glycemia or liver metabolism. The therapeutically effective amount will also vary according to the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained. The dose for oral administration of the compounds according to the invention in human is between 1 to 50 mg/kg, preferably 5 to 20 mg/kg, more preferably 5 to 15 mg/kg, also more preferably about 1 to 10 mg/kg in human. The dose of topical administration of the compounds of the present invention in human is between 0.01 to 10% (w/w), preferably 0.1 to 5% (w/w), and more preferably 1 to 5%. The metabolism of a mouse eliminates any compound faster than human metabolism, such that for testing of a compound in mice, the dose may be multiplied 10 times to 20 times.

As used herein, the term "pharmaceutical composition" refers to the presence of at least one compound according to the invention and a pharmaceutically acceptable vehicle.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (e.g. glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In some embodiments, the composition of the present invention comprises an effective amount of a compound of the formula herein above. Particularly preferred is the sodium salt of 2-[3,5-dipentylphenyl]acetate.

In some embodiments, the invention pertains to pharmaceutical compositions for preventing and/or treating pulmonary fibrosis, liver fibrosis, skin fibrosis, renal fibrosis, pancreas fibrosis, systemic sclerosis, cardiac fibrosis or macular degeneration The compounds of the invention may be formulated prior to administration into pharmaceutical compositions using available techniques and procedures. For instance, the pharmaceutical compositions may be formulated in a manner suitable for administration by topical, oral, intravenous (iv), intramuscular (im), depo-im, subcutaneous (sc), depo-sc, sublingually, intranasal, intrathecal topical or rectal routes.

Preferably, the compound(s) of the invention can be orally administered or topically administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g., an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g., hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical preparation suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). For instance, metal salts of the compounds of this invention are expected to have physical chemical properties amenable with the preparation of fine particles of active pharmaceutical ingredient (API) for administration by inhalation but not the free acid form of these compounds. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention may also be administered topically to a subject, e.g., by the direct laying on or spreading of the composition on the epidermal or epithelial tissue of the subject, or transdermally via a "patch". Such compositions include, for example, lotions, creams, solutions, gels, emulsions and solids. These topical compositions may comprise an effective amount, usually about 0.01% to about 10% (w/w), or from about 0.1% to about 5% (w/w), or from about 1% to about 5% (w/w), of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like. The carrier may include vernix. Topical formulation includes one or more excipients such as, but not limited to, protectives, adsorbents, demulcents, emollients, preservatives, antioxidants, moisturizers, buffering agents, solubilizing agents, skin-penetration agents, and surfactants. Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide. Suitable demulcents include, but are not limited to, benzoin, hydroxypropyl cellulose, hydroxypropyl methylcellulose, and polyvinyl alcohol. Suitable emollients include, but are not limited to, animal and vegetable fats and oils, myristyl alcohol, alum, and aluminum acetate. Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, acetate buffers, citrate buffers, phosphate buffers, lactic acid buffers, and borate buffers. Suitable solubilizing agents include, but are not limited to, quaternary ammonium chlorides, cyclodextrins, benzyl benzoate, lecithin, and polysorbates. Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

Other compositions useful for attaining systemic delivery of the subject agents may include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound according to the present invention may also be administered parenterally, intraperitoneally, intraspinally, or intracerebrally. For such compositions, the compound of the invention can be prepared in glycerol, liquid polyethylene glycols, and mixtures thereof and in oils. Under ordinary conditions of storage and use, this preparation may contain a preservative to prevent the growth of microorganisms.

For the method of prevention/slowing progression/treatment of a fibrotic disease, the method of the present invention may also include co-administration of the at least one compound according to the invention, or a pharmaceutically acceptable salt thereof together with the administration of another therapeutically effective agent for the prevention and/or slowing the progression and/or treatment of a fibrotic disease. Accordingly, the invention also relates to a method for preventing, reducing or eliminating a symptom or complication of any one of the above mentioned disease or condition. The method comprises the administration of a first pharmaceutical composition comprising at least one compound of the invention and a second pharmaceutical composition comprising one or more additional active ingredients to a subject in need thereof, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of formula I. The second agent may be selected from the list of compounds given herein above.

The present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further

EXAMPLES

The examples set forth herein below provide exemplary methods for the preparation of certain representative compounds encompassed by Formula I. Some Examples provide exemplary uses of certain representative compounds of the invention. Also provided are exemplary methods for assaying the compounds of the invention for efficacy.

The examples set forth herein below provide exemplary methods for the preparation of certain representative compounds encompassed by general Formula I. Some Examples provide exemplary uses of certain representative compounds of the invention. Also provided are exemplary methods for assaying the compounds of the invention for in vitro and in vivo efficacy.

Instrumentation:

All HPLC chromatograms and mass spectra were recorded on an HP 1100 LC-MS Agilent instrument using an analytical C18 column (250×4.6 mm, 5 microns) with a gradient over 3 min of 50-99% CH3CN—H2O with 0.01% TFA as the eluant followed by isocratic over 3 min and a flow of 2 mL/min.

Example 1

Experimental Procedure for the Preparation of Sodium 2-[3,5-Dipentylphenyl]Acetate (Compound 1)

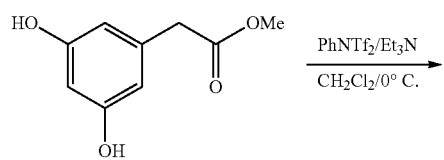

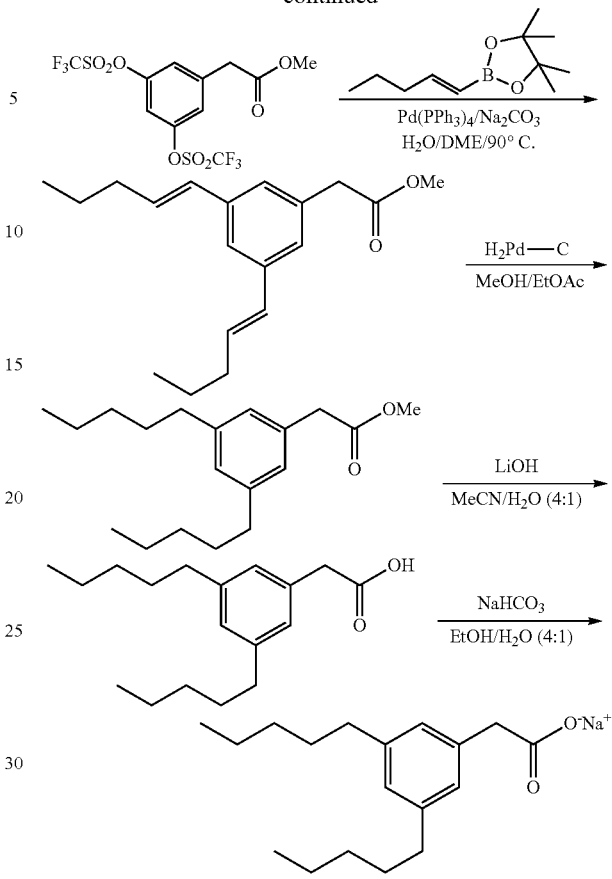

Step 1:

A suspension of methyl 2-[3,5-dihydroxyphenyl]acetate (1.00 g, 5.49 mmol) and N-phenyl-bis(trifluoromethylsulfonyl)imide (4.31 g, 12.1 mmol) in dichloromethane (20 ml), at 0° C. under nitrogen, was treated with triethylamine (1.68 ml, 12.1 mmol). A clear solution formed. The reaction was then stirred under nitrogen at 0° C. for 2 h, and at room temperature for 21 h. The reaction was diluted with ethyl acetate (100 ml), and the solution was washed with 0.5M aqueous sodium hydroxide (2×100 ml), and with saturated aqueous sodium chloride (75 ml); then dried over sodium sulphate; filtered and evaporated in vacuo to give the crude product. Purification on a Biotage™ 40iM column (silica), eluting with ethyl acetate/hexane 0:1 to 1:9, gave methyl 2-[3,5-bis(trifluoromethylsulfonyloxy)phenyl]acetate (2.23 g, 91%) as pale oil. $^1$H NMR (400 MHz, CDCl3): δ 7.32 (d, J=2.2 Hz, 2H), 7.18 (dd, J=2.2, 2.2 Hz, 1H), 3.72 (s, 5H); 19F NMR (377 MHz, CDCl3): δ −73.20 (s, 3F); $^{13}$C NMR (101 MHz, CDCl3): δ 170.05, 149.48, 139.01, 122.95, 118.87 (q, JCF=320.5 Hz), 114.42, 52.62, 40.29.

Step 2:

A solution of the aryl bis(triflate) (2.23 g, 4.99 mmol) and (E)-1-penten-1-ylboronic acid pinacol ester (2.45 g, 12.5 mmol) in 1,2-dimethoxyethane (25 ml) was treated with a solution of sodium carbonate (1.59 g, 15.0 mmol) in water (8 ml). The solution was deoxygenated with nitrogen, and was then treated with Tetrakis(triphenylphosphine) palladium (0.58 g, 0.50 mmol). The mixture was heated at 90° C., in a sealed tube for 17 h. The reaction was cooled to room temperature and was partitioned between ethyl acetate (200 ml) and 1M aqueous hydrochloric acid (150 ml). The organic phase was washed with 5% aqueous sodium bicarbonate (150 ml), and with saturated aqueous sodium chloride (150 ml); then dried over sodium sulphate; filtered, and evaporated in vacuo to give the crude product. Purification on a Biotage™ 40iL column (silica), eluting with ethyl acetate/hexane 0:1 to 3:97, gave methyl 2-[3,5-di[(E)-1-pent-1-enyl]phenyl] acetate as an inseparable 10:4 mixture with excess (E)-1-penten-1-ylboronic acid pinacol ester (1.12 g, 61%). $^1$H NMR (400 MHz, CDCl3): δ 7.21 (s, 1H), 7.10 (d, J=1.3 Hz, 2H), 6.34 (d, J=15.8 Hz, 1H), 6.22 (dd, J=15.8, 6.7 Hz, 1H), 3.65 (s, 3H), 3.55 (s, 2H), 2.18 (tdd, J=6.8, 6.8, 1.0 Hz, 2H), 1.49 (qt, J=7.4, 7.2 Hz, 2H), 0.96 (t, J=7.4 Hz, 3H); $^{13}$C NMR (101 MHz, CDCl3): δ 172.04, 138.59, 134.47, 131.34, 129.97, 125.57, 122.75, 52.07, 41.32, 35.39, 22.77, 13.97.

Step 3:

A solution of the unsaturated compound (1.12 g, 78.5% w/w, 3.07 mmol) in ethyl acetate (1 ml) and methanol (1 ml) was treated with palladium on carbon (10% w/w Pd; 0.12 g). The mixture was degassed with hydrogen, and was stirred under 1 atm. of hydrogen at room temperature for 22 h. The reaction was filtered, and evaporated in vacuo to give methyl 2-[3,5-dipentylphenyl] acetate as an inseparable 10:4 mixture with pentylboronic acid pinacol ester (0.86 g, 76%). $^1$H NMR (400 MHz, CDCl3): δ 6.93 (s, 3H), 3.70 (s, 3H), 3.59 (s, 2H), 2.58 (t, J=7.9 Hz, 2H), 1.58-1.66 (m, 2H), 1.32-1.38 (m, 4H), 0.91 (t, J=6.8 Hz, 3H).

Step 4:

A solution of the methyl ester (0.86 g, 79% w/w, 2.34 mmol) in acetonitrile (24 ml) was treated with a solution of lithium hydroxide (0.28 g, 11.7 mmol) in water (6 ml), and the reaction was stirred at room temperature for 22 h. The reaction was quenched with 1M aqueous hydrochloric acid (55 ml), and then extracted with ethyl acetate (100 ml). The organic extract was washed with saturated aqueous sodium chloride (50 ml); then dried over sodium sulphate; filtered, and evaporated in vacuo to give the crude product. Purification on a SiliaSep silicon oxide column, eluting with ethyl acetate/hexane 0:1 to 1:4, gave 2-[3,5-dipentyl]phenyl] acetic acid as a colorless oil (0.55 g, 84%). $^1$H NMR (400 MHz, CDCl3): δ 6.99 (s, 3H), 3.65 (s, 2H), 2.63 (t, J=7.8 Hz, 2H), 1.64-71 (m, 2H), 1.36-1.44 (m, 4H), 0.97 (t, J=6.9 Hz, 3H); $^{13}$C NMR (101 MHz, CDCl3): δ 178.96, 143.55, 133.21, 127.93, 127.06, 41.47, 36.13, 31.94, 31.47, 22.86, 14.34.

Step 5:

A solution of the acid (0.48 g, 1.75 mmol) in ethanol (12 ml) was treated with a solution of sodium bicarbonate (0.15 g, 1.75 mmol) in water (3 ml), and the reaction was stirred at room temperature for 3 d. Ethanol was evaporated in vacuo, and the residual aqueous syrup was diluted with water (50 ml), filtered (PES, 0.2 μm), and lyophilised to give sodium 2-[3,5-dipentylphenyl] acetate as a white solid (0.52 g, quantitative). mp 225-230° C.; $^1$H NMR (400 MHz, CD3OD+D2O): δ 6.92 (s, 2H), 6.76 (s, 1H), 3.41 (s, 2H), 2.50 (t, J=7.5 Hz, 2H), 1.52-1.59 (m, 2H), 1.23-1.33 (m, 4H), 0.85 (t, J=6.9 Hz, 3H); $^{13}$C NMR (101 MHz, CD3OD+D2O): δ 179.99, 142.66, 137.63, 126.66, 126.16, 45.11, 35.61, 31.36, 31.19, 22.41, 13.47; LRMS (ESI): m/z 277.5 (w, [M-Na++2H+]), 231.1 (100%, tropylium ion from loss of carboxy group); HPLC: 3.0 min.

Compound 2, Sodium Salt of 2-(3,5-Dihexylphenyl)acetic Acid

The above compound was prepared from (E)-hex-1-enylboronic acid pinacol ester as for compound 1. White solid; $^1$H NMR (400 MHz, CD$_3$OD): δ 6.96 (s, 2H), 6.79 (s, 1H), 3.43 (s, 2H), 2.54 (d, J=7.7 Hz, 4H), 1.55-1.63 (m, 4H), 1.28-1.36 (m, 12H), 0.89 (t, J=6.8 Hz, 6H); $^{13}$C NMR (101 MHz, CD$_3$OD): δ 179.68, 142.38, 137.82, 126.55, 126.07, 45.30, 35.87, 31.83, 31.67, 29.02, 22.61, 13.42; LRMS (ESI): m/z 322.0 (100%, M-Na$^+$+H$^+$+NH$_4^+$) and 259.0 (35%, M-CO$_2$Na); UPLC (System A): 8.9 min. UPLC System A: Mobile phase A=10 mM aqueous ammonium bicarbonate; mobile phase B=acetonitrile; solid phase=HSS T3 column; gradient=5-100% B in A over 10 minutes.

Compound 3, Sodium Salt of 2-(2-Hydroxy-3,5-dipentylphenyl)acetic Acid

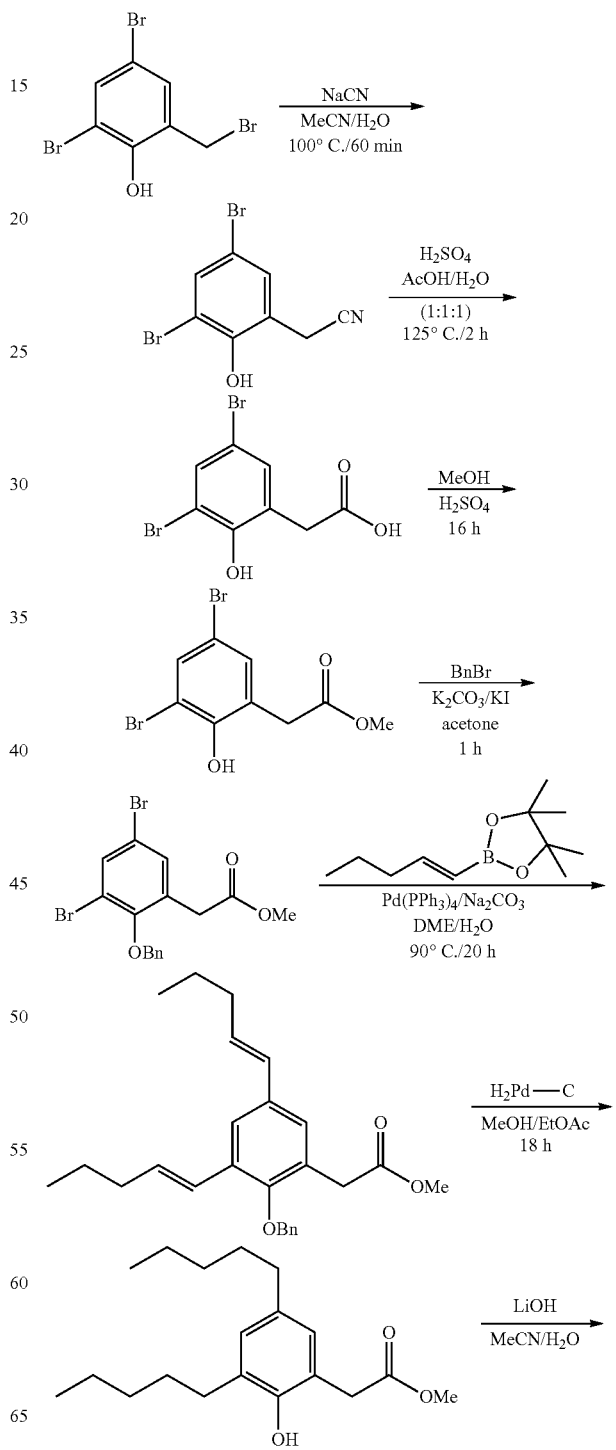

-continued

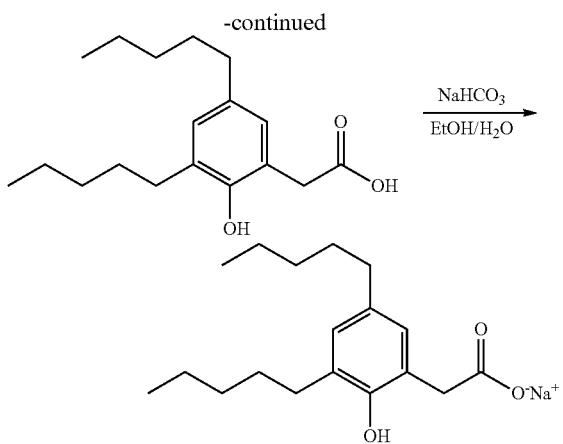

Step 1

A solution of 2,4-dibromo-6-(bromomethyl)phenol (3.5 g, 10.0 mmol) in acetonitrile (17 ml) was treated with a solution of sodium cyanide (2.5 g, 50.0 mmol) and the reaction was heated at 100° C. under reflux for 1 h. The reaction mixture cooled to room temperature and was poured into water (100 ml). The pH was adjusted from 10 to 8 with 1M aqueous hydrochloric acid, and the mixture was extracted with ethyl acetate (3×250 ml). Combined extracts were washed with 1M aqueous hydrochloric acid (250 ml) and with saturated aqueous sodium chloride (250 ml); dried over sodium sulfate; filtered and evaporated in vacuo to give the crude product. Extraction with acetone; filtration; and evaporation in vacuo gave 2-(3,5-dibromo-2-hydroxyphenyl)acetonitrile (2.6 g, 90%). $^1$H NMR (400 MHz, d$_6$-acetone): δ 8.75 (br s, 1H), 7.69 (d, J=2.3 Hz, 1H), 7.54 (d, J=2.3 Hz, 1H), 3.92 (s, 2H); $^{13}$C NMR (101 MHz, d$_6$-acetone): δ 151.31, 134.51, 131.92, 122.80, 117.43, 111.89, 111.53, 18.70.

Step 2

2-(3,5-Dibromo-2-hydroxyphenyl)acetonitrile (2.6 g, 9.0 mmol) was treated with a mixture of sulfuric acid (2.5 ml), acetic acid (2.5 ml) and water (2.5 ml), and the reaction was heated at 125° C. under reflux for 2 h. The reaction mixture was cooled to room temperature and was poured into a mixture of ice (50 ml) and water (50 ml), and was then stirred until the ice had melted. The mixture was extracted with ethyl acetate (250 ml); and the extract was then washed with water (100 ml) and with saturated aqueous sodium chloride (100 ml); dried over sodium sulfate; filtered and evaporated in vacuo to give the crude 2-(3,5-dibromo-2-hydroxyphenyl)acetic acid (3.1 g). This material was used directly in the next step without further purification or characterization.

Step 3

A solution of crude 2-(3,5-dibromo-2-hydroxyphenyl) acetic acid (3.1 g, 9.0 mmol) in methanol (17 ml) was treated with sulfuric acid (0.43 ml, 8.1 mmol) and the reaction was stirred at ambient temperature for 16 h. Methanol was evaporated in vacuo, and the residue was dissolved in ethyl acetate (270 ml). The solution was washed with water (2×200 ml) and with saturated aqueous sodium chloride (130 ml); dried over sodium sulfate; filtered and evaporated in vacuo to give the crude product. Purification on a Biotage™ SP1 system (120 g silica cartridge), eluting with 0-20% ethyl acetate in hexanes, gave methyl 2-(3,5-dibromo-2-hydroxyphenyl)acetate (1.4 g, 49%). $^1$H NMR (400 MHz, CDCl$_3$): δ 7.52 (d, J=2.2 Hz, 1H), 7.23 (d, J=2.2 Hz, 1H), 6.42 (br s, 1H), 3.72 (s, 3H), 3.65 (s, 2H); $^{13}$C NMR (101 MHz, CDCl$_3$): δ 172.06, 150.60, 133.74, 133.50, 123.94, 112.62, 111.77, 52.78, 36.61.

Step 4

A solution of methyl 2-(3,5-dibromo-2-hydroxyphenyl) acetate (0.5 g, 1.54 mmol) in acetone (5 ml) was treated with potassium carbonate (0.26 g, 1.86 mmol), potassium iodide (0.05 g, 0.32 mmol) and benzyl bromide (0.20 ml, 1.7 mmol), and the reaction was stirred at room temperature for 1 h. Acetone was evaporated in vacuo, and the residue was partitioned between ethyl acetate (50 ml) and 1M aqueous hydrochloric acid (50 ml). The organic phase was washed with saturated aqueous sodium chloride (50 ml); dried over sodium sulfate; filtered and evaporated in vacuo to give the crude product. Purification on a Biotage™ SP1 system (40 g silica cartridge), eluting with 0-10% ethyl acetate in hexanes, gave methyl 2-(2-(benzyloxy)-3,5-dibromophenyl) acetate (0.6 g, 95%). $^1$H NMR (400 MHz, CDCl$_3$): δ 7.67 (d, J=2.4 Hz, 1H), 7.48-7.51 (m, 2H), 7.37 (d, J=2.4 Hz, 1H), 7.34-7.43 (m, 3H), 4.99 (s, 2H), 3.66 (s, 3H), 3.60 (s, 2H); $^{13}$C NMR (101 MHz, CDCl$_3$): δ 171.26, 153.79, 136.56, 135.38, 133.57, 132.04, 128.82, 128.64, 128.52, 118.69, 117.56, 75.53, 52.50, 35.86.

Step 5

Methyl 2-(2-(benzyloxy)-3,5-dibromophenyl)acetate (0.3 g, 0.73 mmol) and (E)-pent-1-enylboronic acid pinacol ester (0.4 g, 1.79 mmol) were coupled as for Compound I, step 2, to give methyl 2-(2-(benzyloxy)-3,5-di((E)-pent-1-enyl) phenyl)acetate (0.21 mg, 72%). $^1$H NMR (400 MHz, CDCl$_3$): δ 7.50 (d, J=7.2 Hz, 2H), 7.44 (dd, J=7.2, 7.2 Hz, 2H), 7.43 (d, J=2.1 Hz, 1H), 7.38 (dd, J=7.2, 7.2 Hz, 1H), 7.18 (d, J=2.1 Hz, 1H), 6.72 (d, J=15.8 Hz, 1H), 6.39 (d, J=15.8 Hz, 1H), 6.32 (dt, J=15.8, 7.0 Hz, 1H), 6.22 (dt, J=15.8, 6.8 Hz, 1H), 4.87 (s, 2H), 3.69 (s, 3H), 3.67 (s, 2H), 2.20-2.29 (m, 4H), 1.50-1.60 (m, 4H), 1.01 (t, J=7.3 Hz, 3H), 1.00 (t, J=7.4 Hz, 3H); $^{13}$C NMR (101 MHz, CDCl$_3$): δ 172.49, 153.59, 137.58, 134.35, 132.91, 131.91, 130.84, 129.53, 128.78, 128.32, 128.30, 128.24, 127.26, 125.21, 123.89, 75.89, 52.21, 35.94, 35.74, 35.42, 22.87, 22.77, 14.07, 14.06.

Step 6

Methyl 2-(2-(benzyloxy)-3,5-di((E)-pent-1-enyl)phenyl) acetate (0.2 g, 0.53 mmol) was hydrogenated as for Compound I, step 3, to give methyl 2-(2-hydroxy-3,5-dipentylphenyl)acetate (0.12 g, 73%). $^1$H NMR (400 MHz, CDCl$_3$): δ 7.37 (s, 1H), 6.92 (d, J=2.1 Hz, 2H), 6.77 (d, J=2.1 Hz, 1H), 3.76 (s, 3H), 3.67 (s, 2H), 2.65 (t, J=7.8 Hz, 2H), 2.51 (t, J=7.8 Hz, 2H), 1.58-1.66 (m, 4H), 1.31-1.41 (m, 8H), 0.93 (t, J=7.0 Hz, 3H), 0.92 (t, J=6.9 Hz, 3H); $^{13}$C NMR (101 MHz, CDCl$_3$): δ 175.01, 151.27, 135.14, 131.48, 129.92, 128.52, 120.30, 52.95, 38.35, 35.34, 32.15, 31.86, 31.74, 30.61, 30.03, 22.87, 22.83, 14.34, 14.31.

Step 7

Methyl 2-(2-hydroxy-3,5-dipentylphenyl)acetate (0.2 g, 0.53 mmol) was hydrolysed as for Compound I, step 4, to give the crude product mixed with lactonised material. A small portion was purified on a Biotage™ SP1 system (120 g silica cartridge), eluting with 0-100% ethyl acetate in hexanes, to give 2-(2-hydroxy-3,5-dipentylphenyl)acetic acid (13.5 mg). $^1$H NMR (400 MHz, CDCl$_3$): δ 10.5 (br s, 1H), 6.89 (d, J=2.2 Hz, 1H), 6.78 (d, J=2.2 Hz, 1H), 6.32 (br s, 1H), 3.66 (s, 2H), 2.58 (t, J=7.9 Hz, 2H), 2.48 (t, J=7.8 Hz, 2H), 1.52-1.63 (m, 4H), 1.26-1.37 (m, 8H), 0.90 (t, J=7.0 Hz, 3H), 0.88 (t, J=6.8 Hz, 3H).

Step 8

2-(2-Hydroxy-3,5-dipentylphenyl)acetic acid (13.5 mg, 0.046 mmol) was converted to the sodium salt as for Compound I, step 5 to give sodium 2-(2-hydroxy-3,5-dipentylphenyl)acetate (11 mg, 77%). $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.6 Hz, 2H), 1.50-1.61 (m, 4H), 1.25-1.37 (m, 8H), 0.90 (t, J=6.8 Hz, 3H), 0.88 (t, J=7.0 Hz, 3H); $^{13}$C NMR (101 MHz, CD$_3$OD): δ 180.33, 151.94, 133.47, 130.37, 128.21, 127.81, 123.99, 42.90, 34.97, 31.81, 31.60, 31.40, 30.25, 29.88, 22.51, 22.45, 13.29, 13.24; LRMS (ESI negative): m/z 291.2 (100%, M-Na$^+$); UPLC (System B): 7.7 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound 4, Sodium Salt of 2-(3,5-Dihexyl-2-hydroxyphenyl)acetic Acid

The above compound was prepared as for Compound 3, using (E)-hex-1-enylboronic acid pinacol ester. $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.80 Hz, 3H); LRMS (ESI negative): m/z 319 (100%, M-Na$^+$); UPLC (System B): 8.7 min. ULC System B: Mobile phase A=0.1% aqueous formic acid; mobile phase B=0.1% formic acid in acetonitrile; solid phase=HSS T3 column; gradient =5-100% B in A over 10 minutes.

Compound 5, Sodium Salt of 2-(4-Hydroxy-3,5-dipentylphenyl)acetic Acid

The above compound was prepared as for Compound 3 from 2-(3,5-dibromo-4-hydroxyphenyl)acetic acid. $^1$H NMR (400 MHz, CD$_3$OD): δ 6.87 (s, 2H), 3.33 (s, 2H), 2.55 (t, J=7.7 Hz, 4H), 1.53-1.61 (m, 4H), 1.31-1.37 (m, 8H), 0.90 (t, J=7.0 Hz, 6H); LRMS (ESI negative): m/z 291.1 (100%, M-Na$^+$); UPLC (System B): 6.8 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound 6, Sodium Salt of 2-(3,5-Dihexyl-4-hydroxyphenyl)acetic Acid

The above compound was prepared as for Compound 3, from 2-(3,5-dibromo-4-hydroxyphenyl)acetic acid, and (E)-hex-1-enylboronic acid pinacol ester. $^1$H NMR (400 MHz, CD$_3$OD): δ 6.72 (d, J=2.0 Hz, 1H), 6.69 (d, J=2.0 Hz, 1H), 3.46 (s, 2H), 2.56 (t, J=7.6 Hz, 2H), 2.44 (t, J=7.5 Hz, 2H), 1.50-1.60 (m, 4H), 1.27-1.37 (m, 12H), 0.89 (t, J=6.6 Hz, 3H), 0.88 (t, J=6.8 Hz, 3H); LRMS (ESI negative): m/z 319.1 (100%, M-Na$^+$); UPLC (System B): 7.6 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound 7, Sodium Salt of 2-(4-Fluoro-3,5-dihexylphenyl)acetic Acid

The above compound was prepared as for Compound 3, starting from 3,5-dibromo-4-fluorobenzyl bromide and (E)-hex-1-enylboronic acid pinacol ester. 3,5-Dibromo-4-fluorobenzyl bromide was prepared by bromination of 3,5-dibromo-4-fluorotoluene with N-bromosuccinimide and azobisisobutyronitrile in acetonitrile at 80° C. $^1$H NMR (400 MHz, CD$_3$OD): δ 6.98 (d, J$_{HF}$=7.0 Hz, 2H), 3.38 (s, 2H), 2.57 (t, J=7.7 Hz, 4H), 1.54-1.61 (m, 4H), 1.28-1.37 (m, 12H), 0.89 (t, J=6.7 Hz, 6H); $^{19}$F NMR (377 MHz, CD$_3$OD): δ −132.17 (d, J$_{HF}$=6.6 Hz, 1F); $^{13}$C NMR (101 MHz, CD$_3$OD): δ 179.44, 158.11 (d, J$_{CF}$=239.8 Hz), 133.26 (d, J$_{CF}$=3.8 Hz), 128.73 (d, J$_{CF}$=5.4 Hz), 128.56 (d, J$_{CF}$=16.9 Hz), 44.52, 31.69, 30.35 (d, J$_{CF}$=1.5 Hz), 28.98, 28.97 (d, J$_{CF}$=3.1 Hz), 22.51, 13.29; LRMS (ESI negative): m/z 321.0 (100%, M-Na$^+$); UPLC (System B): 9.2 min. UPLC System B: Mobile phase A=0.1% aqueous formic acid; mobile phase B=0.1% formic acid in acetonitrile; solid phase=HSS T3 column; gradient=5-100% B in A over 10 minutes.

Compound 8, Sodium Salt of 2-(4-Fluoro-3,5-dipentylphenyl)acetic Acid

The above compound was prepared as for Compound 3, starting from 3,5-dibromo-4-fluorobenzyl bromide. $^1$H NMR (400 MHz, CD$_3$OD): δ 6.98 (d, J$_{HF}$=6.8 Hz, 2H), 3.37 (s, 2H), 2.57 (t, J=7.6 Hz, 4H), 1.54-1.62 (m, 4H), 1.28-1.37 (m, 8H), 0.90 (t, J=7.0 Hz, 6H); $^{19}$F NMR (377 MHz, CD$_3$OD): δ −132.34 (d, J$_{HF}$=6.6 Hz, 1F); $^{13}$C NMR (101 MHz, CD$_3$OD): δ 179.41, 158.10 (d, J$_{CF}$=239.8 Hz), 133.26 (d, J$_{CF}$=3.8 Hz), 128.72 (d, J$_{CF}$=4.6 Hz), 128.56 (d, J$_{CF}$=16.9 Hz), 44.51, 31.54, 30.07, 28.92 (d, J$_{CF}$=3.1 Hz), 22.38, 13.22; LRMS (ESI negative): m/z 293.0 (100%, M-Na$^+$); UPLC (System B): 8.4 min. UPLC System B: Mobile phase A=0.1% aqueous formic acid; mobile phase B=0.1% formic acid in acetonitrile; solid phase=HSS T3 column; gradient=5-100% B in A over 10 minutes.

Example 2

Antifibrotic Effect of Compounds of the Present Invention on the Fibrotic Markers α-SMA and Collagen 1 in TGF-β Induced Fibroblast and Epithelial Cells Fibrosis is a chronic and progressive process characterized by an excessive accumulation of extracellular matrix (ECM) leading to stiffening and/or scarring of the involved tissue. It develops through complex cell, extracellular matrix, cytokine and growth factor interactions. Distinct cell types are involved such as resident mesenchymal cells (fibroblasts and myofibroblasts) and ECM-producing cells derived from epithelial and endothelial cells (through a process termed epithelial- and endothelial-mesenchymal transition), local or bone marrow-derived stem cells (fibrocytes). Myofibroblasts has long been regarded as a major cell type involved in normal wound healing, and as the key effector cell in fibrogenesis. They are highly synthetic for collagen and other ECM components, and are characterized by the de novo expression of α-smooth muscle actin (α-SMA) (reviewed in Scotton C. J. and Chambers R. C., 2007). The presence of myofibroblasts in fibrotic lesions in animal models of fibrosis correlates with the development of active fibrosis, and their persistence and localization to fibrotic foci in human disease is associated with disease progression (Kuhn C. and McDonald J. A., 1991, and Zhang et al., 1994). Myofibroblasts also exhibit an enhanced migratory phenotype (Suganuma et al. 1995) and are capable of releasing numerous pro-fibrotic mediators.

In fibroblast, analysis was undertaken to determine the effect of preferred compounds of the present invention on TGF-β-induced α-SMA (marker of fibrosis) mRNA expression on normal rat kidney fibroblast (NRK-49F). NRK-49F were treated with TGF-β at a concentration of 10 ng/ml and became activated (myofibroblast) and expressed α-SMA. Expression of the profibrotic marker α-SMA was determined by quantitative real-time PCR. As shown in Table 2, the compounds of the invention inhibit the expression of α-SMA in TGF-β-induced NRK-49F cells.

TABLE 2

Inhibition of α-SMA mRNA expression by compounds in TGF-β induced NRK-49F cells

| Compound | Structure | α-SMA expression in NRK-49F<br>% of inhibition<br>[mM] |
|---|---|---|
| 1 | 3,5-dipentylphenylacetate sodium salt | 94%<br>[0.01] |
| 2 | 3-pentyl-5-hexylphenylacetate sodium salt | 89%<br>[0.006] |
| 3 | 3,5-dipentyl-2-hydroxyphenylacetate sodium salt | 100%<br>[0.0125] |
| 5 | 3,5-dipentyl-4-hydroxyphenylacetate sodium salt | 41%<br>[0.025] |

The role of EMT during tissue injury leading to organ fibrosis (deposition of collagens, elastin, tenacin, and other matrix molecules) is becoming increasingly clear. A great bulk of such evidence exists for EMT associated with progressive kidney diseases, lung, skin, heart and liver. For example, in kidney, emerging evidence suggests that renal tubular epithelial cells can undergo epithelial to mesenchymal transition (EMT) to become matrix-producing fibroblasts under pathologic conditions (Strutz F., Müller G. A., 2000; and Yang J., Liu Y., 2001). This phenotypic conversion not only illustrates the remarkable plasticity of mature, differentiated kidney epithelial cells, but is also fundamentally implicated in the pathogenesis of a wide range of chronic renal diseases (Iwano M. et al., 2002; Yang J. et al., 2002; Zeisberg M. et al., 2001; and Yang J., Liu Y., 2002). Recent studies provide compelling evidence that a large proportion of the interstitial fibroblasts in fibrotic kidneys originate from tubular epithelial cells via EMT (Iwano M. et al., 2002). Likewise, selective blockade of tubular EMT, due to preservation of tubular basement membrane integrity in tPA-/- mice, protects the kidney from developing fibrotic lesions after obstructive injury (Yang J. et al., 2002). These observations underscore the crucial importance of tubular EMT in the onset and progression of chronic renal fibrosis that eventually results in end-stage renal failure. Several factors have been suggested as potential initiators of EMT in different in vitro and in vivo models (Yang J, Liu Y., 2001; Kalluri R., Neilson E. G., 2003; Okada H. et al., 1997; Fan J. M. et al., 2001; Strutz F. et al., 2002; Ha H., Lee H. B., 2003; Lan H. Y., 2003; Lee J. M. et al., 2006; and Zavadil J., Böttinger E. P., 2005). With the exception of CTGF, each of these mediators requires the induction of TGF-β to complete the process of EMT (Yang J., Liu Y., 2001; Liu Y., 2004; and Lan H. Y., 2003).

In epithelial cells, analysis was undertaken to determine the effect of compounds of the invention on TGF-β-induced collagen 1 (marker of fibrosis) on human proximal tubule epithelial cells (HK-2). HK-2 cells are immortalized proximal tubule epithelial cells, from human kidney, which were treated with TGF-β at a concentration of 10 ng/mL Expression of the profibrotic marker collagen 1 was determined by quantitative real-time PCR. As shown in Table 3, Compound 1 and 2 inhibits the expression of collagen in TGF-β-induced HK-2 cells.

TABLE 3

Inhibition of collagen mRNA expression in TGF-β induced HK-2 epithelial cells

| Compound | Structure | Collagen expression in HK-2 cells % of inhibition [mM] |
|---|---|---|
| 1 | (structure: 3,5-dipentylphenylacetic acid sodium salt) | 100% [0.02] |
| 2 | (structure: 3,5-dihexylphenylacetic acid sodium salt) | 100% [0.008] |

Example 3

Antifibrotic Effect of Compounds of the Invention on Skin Fibrosis

The effect of Compound 1 of the invention on skin fibrosis was also studied using normal human dermal fibroblasts (NHDF).

In vitro analysis was undertaken to determine the effect of Compound I on TGF-β-induced CTGF and α-SMA (markers of fibrosis) on normal human dermal fibroblasts (NHDF).

Expression of the profibrotic (CTGF) and fibrotic markers (α-SMA) were determined by quantitative real-time PCR. As shown in Table 4, Compound 1 inhibits by 99 and 85% the expression of mRNA of α-SMA and CTGF, respectively.

TABLE 4

Inhibition of α-SMA and CTGF mRNA expression in TGF-β induced NHDF cells.

| Compound | Structue | α-SMA expression in NHDF cells % of inhibition [mM] | CTGF expression in NHDF cells % of inhibition [mM] |
|---|---|---|---|
| 1 | (structure: 3,5-dipentylphenylacetic acid sodium salt) | 99% [0.02] | 85% [0.02] |

Example 4

Antifibrotic Activity of Compound 1 in a Model of Renal Fibrosis

Typical experimental models of kidney fibrosis in mice or rats include db/db nephritic mice (models for diabetic nephropathy) and reflects the nephropathy observed in human. Evaluation of the effect of Compound 1 on diabetic nephropathy was performed in a db/db mouse model. Briefly, total nephrectomy of the right kidney was performed on day 0 and db/db mice (6-week old) were treated with vehicle or Compound 1 (10 and 50 mg/kg, oral once a day) from day 1 and glomerular filtration rate (GFR) was measured on day 119 as a direct measure of kidney function. FIG. 1 illustrates the reduction of GFR in db/db diabetic mouse compared to C57BL/6 mice (control mice), showing clearly the nephropathy associated with diabetes. Oral treatment with 10 and 50 mg/kg increases the GFR function of the kidney up to normal (C57BL/6) mouse, as shown in FIG. 1. This result clearly indicates that the treatment with Compound 1 reduces nephropathy and fibrosis of the kidney of the diabetic db/db mice.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A kit for preventing and/or slowing progression of and/or treating fibrotic disease in a subject in need thereof, wherein said kit comprises (a) a pharmaceutically acceptable salt of a compound of the formula:

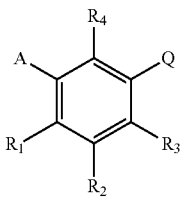

wherein
A is straight $C_5$ alkyl, straight $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_1$ is H, F or OH;
$R_2$ is straight $C_5$ alkyl, straight $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;
$R_3$ is H, F, OH or $CH_2Ph$;
$R_4$ is H, F or OH;
Q is
1) $(CH_2)_m C(O)OH$ wherein m is 1 or 2,
2) $CH(CH_3)C(O)OH$,
3) $C(CH_3)_2 C(O)OH$,
4) CH(F)—C(O)OH,
5) $CF_2$—C(O)OH, or
6) C(O)—C(O)OH;
and wherein the pharmaceutically acceptable salt of said compound is sodium, potassium, lithium, ammonium, calcium, magnesium, manganese, zinc, iron, or copper; and
(b) instructions for administering a therapeutically effective amount of the pharmaceutically acceptable salt to the subject suffering from said fibrotic disease.

2. The kit of claim 1, wherein the fibrotic disease is pulmonary fibrosis, liver fibrosis, skin fibrosis, renal fibrosis, pancreas fibrosis, systemic sclerosis, cardiac fibrosis or macular degeneration.

3. The kit of claim 1, comprising instructions for administering between about 1 to about 50 mg/kg of the pharmaceutically acceptable salt daily and orally to the subject who is a human.

4. The kit of claim 1, comprising instructions for administering between about 0.01 to about 10% (w/w) of the pharmaceutically acceptable salt daily and topically to the subject who is a human, and wherein the fibrotic disease is skin fibrosis.

5. The kit of claim 1, wherein the fibrotic disease is pulmonary fibrosis.

6. The kit of claim 1, wherein the fibrotic disease is liver fibrosis.

7. The kit of claim 1, wherein the fibrotic disease is skin fibrosis.

8. The kit of claim 1, wherein the fibrotic disease is cardiac fibrosis.

9. The kit of claim 1, wherein the fibrotic disease is renal fibrosis.

10. The kit of claim 4, wherein the concentration of the pharmaceutically acceptable salt is between about 0.1 to about 5% (w/w).

11. The kit of claim 10, wherein the concentration of the pharmaceutically acceptable salt is between about 1 to about 5% (w/w).

12. The kit of claim 1, wherein the pharmaceutically acceptable salt of said compound is sodium.

13. The kit of claim 1, wherein said pharmaceutically acceptable salt is a pharmaceutically acceptable salt of one of the following compounds:

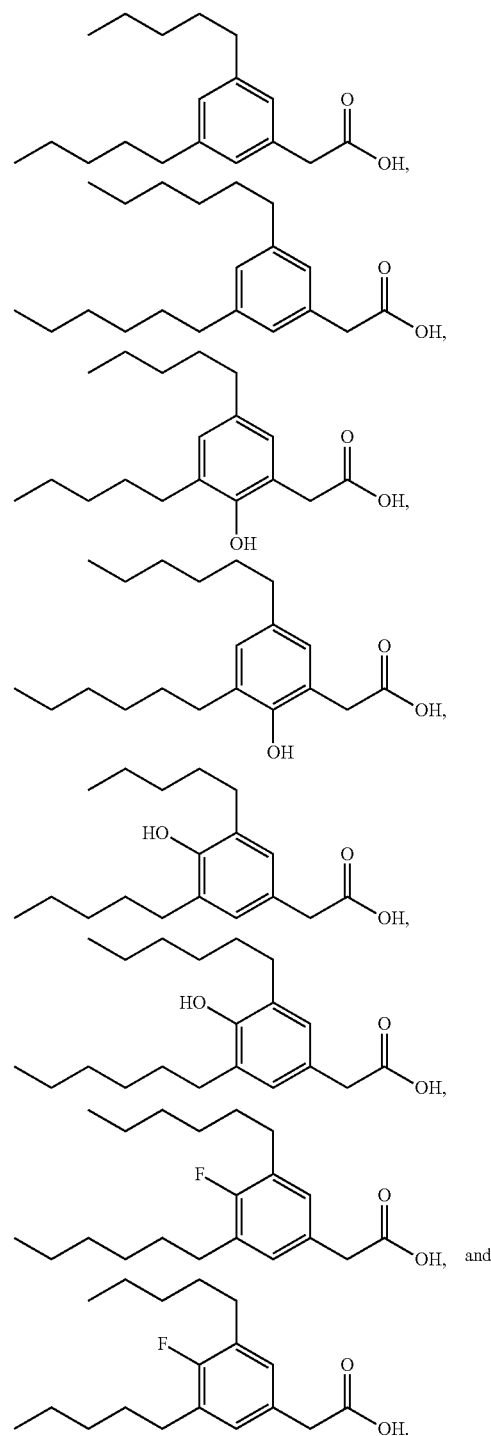

14. The kit of claim 1, wherein Q is $(CH_2)C(O)OH$.

15. The kit of claim 1, wherein A and $R_2$ are straight $C_5$ alkyl.

16. The kit of claim 1, wherein $R_1$ is H and $R_3$ is H.

17. The kit of claim 1, wherein $R_4$ is H or OH.

18. The kit of claim 13, wherein said pharmaceutically acceptable salt is a pharmaceutically acceptable salt of the following compound
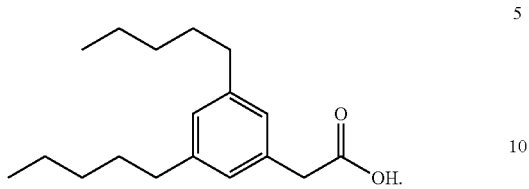
19. The kit of claim 13, wherein said pharmaceutically acceptable salt is a pharmaceutically acceptable salt of the following compound
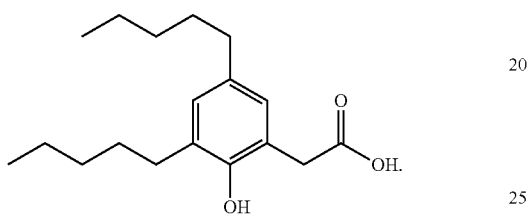
* * * * *